(12) United States Patent
Leong

(10) Patent No.: US 6,712,792 B2
(45) Date of Patent: Mar. 30, 2004

(54) FLASHBACK BLOOD COLLECTION NEEDLE

(75) Inventor: Alvin Tan Chee Leong, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/337,087

(22) Filed: Jan. 6, 2003

(65) Prior Publication Data

US 2003/0105414 A1 Jun. 5, 2003

Related U.S. Application Data

(63) Continuation-in-part of application No. 09/847,732, filed on May 2, 2001.

(30) Foreign Application Priority Data

Nov. 11, 2002 (SG) .......................................... 200206789

(51) Int. Cl.⁷ .............................................. A61M 5/178
(52) U.S. Cl. .................................. 604/168.01; 600/578
(58) Field of Search ....................... 604/168.01, 168.07, 604/93.01, 500; 600/578

(56) References Cited

U.S. PATENT DOCUMENTS

| 3,382,865 A | 5/1968 | Worrall, Jr. |
|---|---|---|
| 3,585,984 A | 6/1971 | Buchanan |
| 3,664,879 A | 5/1972 | Olsson |
| 3,817,240 A | 6/1974 | Ayres |
| 3,874,367 A | 4/1975 | Ayres |
| 3,886,930 A | 6/1975 | Ryan |
| 4,106,497 A | 8/1978 | Percarpio |
| 4,108,175 A | 8/1978 | Orton |
| 4,154,229 A | 5/1979 | Nugent |
| 4,166,450 A | 9/1979 | Abramson |
| 4,193,400 A | 3/1980 | Loveless et al. |
| 4,207,870 A | 6/1980 | Eldridge |
| 4,269,186 A | 5/1981 | Loveless et al. |
| 4,312,362 A | 1/1982 | Kaufman |
| 4,317,445 A | 3/1982 | Robinson |

(List continued on next page.)

FOREIGN PATENT DOCUMENTS

| EP | 0 060 385 | 2/1982 |
|---|---|---|
| EP | 0 139 872 | 7/1984 |
| JP | 58-183172 | 10/1983 |
| JP | 58-188460 | 11/1983 |

(List continued on next page.)

*Primary Examiner*—Edward K. Look
*Assistant Examiner*—Thor Campbell

(57) ABSTRACT

A needle assembly includes a transparent or translucent housing with a fluid inlet end, a fluid outlet end and a flashback chamber therebetween. Substantially axially aligned inlet and outlet cannulas extend from the housing and communicate with the chamber. The external end of the outlet cannula is covered by a sealable sleeve. Relative volumes of the cannulas, the chamber and the sleeve are selected to provide rapid reliable flashback indicative of venous entry.

17 Claims, 10 Drawing Sheets

U.S. PATENT DOCUMENTS

| | | |
|---|---|---|
| 4,340,068 A | 7/1982 | Kaufman |
| 4,398,544 A | 8/1983 | Nugent et al. |
| 4,409,990 A | 10/1983 | Mileikowsky |
| 4,412,548 A | 11/1983 | Hoch |
| 4,416,290 A | 11/1983 | Lutkowski |
| 4,416,291 A | 11/1983 | Kaufman |
| 4,418,703 A | 12/1983 | Hoch et al. |
| 4,436,098 A | 3/1984 | Kaufman |
| 4,444,203 A | 4/1984 | Engelman |
| 4,679,571 A | 7/1987 | Frankel et al. |
| 4,788,986 A | 12/1988 | Harris |
| 4,844,089 A | 7/1989 | Roberti |
| 4,865,592 A | 9/1989 | Rycroft |
| 4,886,072 A | 12/1989 | Percarpio et al. |
| 4,894,052 A | 1/1990 | Crawford |
| 4,971,068 A | 11/1990 | Sahi |
| 5,030,207 A | 7/1991 | Mersch et al. |
| 5,032,116 A | 7/1991 | Peterson et al. |
| 5,033,476 A | 7/1991 | Kasai |
| 5,069,225 A | 12/1991 | Okamura |
| 5,092,845 A | 3/1992 | Chang |
| 5,112,327 A | 5/1992 | Iinuma et al. |
| 5,120,319 A | 6/1992 | Van Heugten et al. |
| 5,122,121 A | 6/1992 | Sos et al. |
| 5,137,518 A | 8/1992 | Mersch |
| 5,181,523 A | 1/1993 | Wendelborn |
| 5,201,794 A | 4/1993 | Kasai et al. |
| 5,217,025 A | 6/1993 | Okamura |
| 5,222,502 A | 6/1993 | Kurose |
| 5,242,411 A | 9/1993 | Yamamoto et al. |
| 5,290,246 A | 3/1994 | Yamamoto et al. |
| 5,295,969 A | 3/1994 | Fischell et al. |
| 5,303,713 A | 4/1994 | Kurose |
| 5,306,259 A | 4/1994 | Fischell et al. |
| 5,496,281 A | 3/1996 | Krebs |
| 5,520,193 A | 5/1996 | Suzuki et al. |
| 5,542,932 A | 8/1996 | Daugherty |
| 5,697,914 A | 12/1997 | Brimhall |
| 5,755,701 A | 5/1998 | Sarstedt |
| 5,830,190 A | 11/1998 | Howell |
| 5,893,844 A | 4/1999 | Misawa |
| 5,984,895 A | 11/1999 | Padilla et al. |
| 6,096,006 A | 8/2000 | Sarstedt et al. |
| 6,110,160 A | 8/2000 | Farber |
| 6,156,010 A | 12/2000 | Kuracina et al. |
| 6,190,370 B1 | 2/2001 | Tsui |
| 6,261,263 B1 | 7/2001 | Huet et al. |

FOREIGN PATENT DOCUMENTS

| | | |
|---|---|---|
| JP | 58-212454 | 12/1983 |
| JP | 4-132541 | 5/1992 |
| JP | 4-364831 | 12/1992 |
| JP | 6-7330 | 1/1994 |
| JP | 7-13304 | 1/1995 |
| JP | 8-150134 | 6/1996 |
| JP | 8-257018 | 10/1996 |
| JP | 8-275933 | 10/1996 |
| JP | 11-28200 | 2/1999 |
| JP | 11-169359 | 6/1999 |
| JP | 11169359 | 6/1999 |
| JP | 2000-139879 | 5/2000 |
| JP | 2000-166903 | 6/2000 |
| JP | 2001-424 | 1/2001 |
| JP | 2001-299728 | 10/2001 |
| JP | 2001-299729 | 10/2001 |

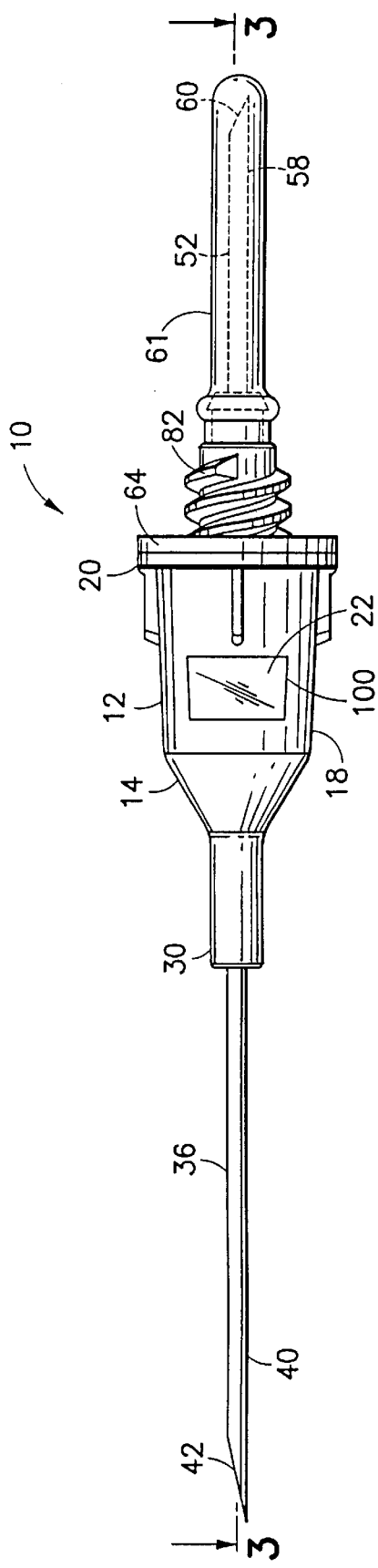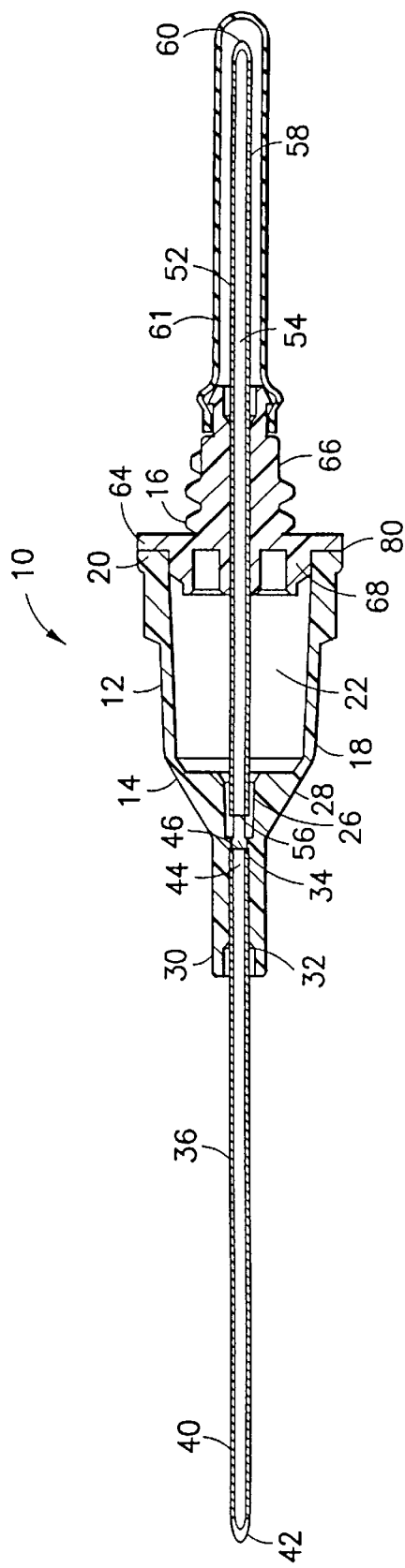
FIG.2
FIG.3

FLASHBACK BLOOD COLLECTION NEEDLE

RELATED APPLICATIONS

This application is a continuation-in-part of U.S. patent application Ser. No. 09/847,732 filed May 2, 2001.

BACKGROUND OF THE INVENTION

1. Field of the Invention

The present invention relates to a device for collecting blood samples by performing venipuncture on a patient. More particularly, the present invention relates to a needle assembly for multiple sample blood collection that allows a phlebotomist to determine whether vein entry has occurred when collecting a blood sample from a patient into an evacuated blood collection tube.

2. Description of Related Art

Venipuncture is the primary method used for acquiring blood samples for laboratory testing. In performing venipuncture procedures, a phlebotomist must follow several steps simultaneously. Such steps include assessing the patient's overall physical and psychological condition so as to properly select a venipuncture site and technique. The phlebotomist must also select the proper corresponding equipment, perform the technique so as to control bleeding, and properly collect and identify fluid specimens for testing. The phlebotomist must ascertain all of these coinciding factors, as such factors may adversely affect the distension of the vein and the length of the venipuncture procedure.

Various venipuncture devices have been developed to address the above-described problems. These devices include a needle assembly with a housing that defines a chamber therein. A single cannula pointed at both ends, is affixed to the housing. The intravenous end of the cannula is adapted for penetration of a patient's vein. The non-patient end of the cannula has a sealable sleeve and is adapted for penetration of a penetrable stop positioned within an evacuated container.

Upon vein entry with the intravenous end of the cannula, blood will flow through the cannula, into the sealable sleeve and into the housing chamber, which is clear or translucent for visualization ("flashback"). Once air is vented from the housing chamber, the blood therein is pressurized each time the sealable sleeve is pushed toward the housing chamber upon activation of an evacuated container.

Due to the length of time between vein entry and flashback, the phlebotomist erroneously believes that satisfactory vein entry has not been achieved since there is no immediate indication of vein entry in the see-through chamber. Often the phlebotomist unnecessarily repeats the venipuncture procedure, requiring replacement of the evacuated container and/or the needle assembly itself. Such a repetitive process prolongs the physical and emotional discomfort endured by the patient. In such cases, a phlebotomist may use a blood collection set to provide some entry indication, and will then incur the cost of the blood collection set, as well as the cost of a discard tube.

It is therefore desirable to provide a fast, accurate and cost effective solution to conventional blood collection procedures upon which the phlebotomist may consistently rely on flashback to provide satisfactory venous entry. Moreover, it is particularly desirable to provide a blood collection device that permits blood flow through a relatively short needle directly into a flashback chamber, thereby providing immediate indication of successful vein entry.

SUMMARY OF THE INVENTION

The present invention provides a needle assembly for the extraction of at least one fluid sample into an evacuated container for laboratory testing. The needle assembly provides a clear or translucent housing chamber with sufficient dead space for blood to flow into the chamber for visualization by the user to confirm successful vein entry.

A needle assembly is provided for collecting at least one fluid sample from a patient for subsequent discharge into at least one evacuated container. The needle assembly of the present invention includes a transparent or translucent housing having a fluid inlet end defined by a cylindrical exterior wall. The wall delineates an annular flashback chamber within the housing for retention of a blood sample therein. The housing further includes a fluid outlet end in communication with said fluid inlet end. A first cannula in fluid communication with the blood inlet end extends outwardly therefrom. The first cannula has an interior extremity positioned proximate the chamber and an exterior extremity opposed thereto that is adapted for puncture of a patient's vein. Similarly, a second cannula is provided in fluid communication with the fluid outlet end and extends outwardly therefrom. The second cannula has an interior extremity positioned proximate the first interior extremity and further includes an exterior extremity opposed to said second interior extremity. The second exterior extremity is adapted for puncture of a penetrable stopper in an evacuated container. The first and second cannula are preferably in axial alignment with one another to provide an axial fluid flow path therebetween along a length of the housing. The second cannula further includes a sealable sleeve. The volumes defined by the lumens through the cannulas, the chamber and the sleeve are selected to achieve a very rapid indication of vein entry while avoiding the need for both a sealable vent or plug and a discard tube.

DESCRIPTION OF THE DRAWINGS

FIG. 2 is a side view of the needle assembly of FIG. 1.

FIG. 3 is a side cross-sectional view of the needle assembly of FIG. 2 taken along 3—3 thereof.

DETAILED DESCRIPTION

The present invention provides a needle assembly for blood collection that provides a visual indication of vein entry ("flashback") upon collection of a blood or other fluid sample from a patient into one or more evacuated blood collection tubes.

As illustrated in FIGS. 1–4, a needle assembly 10 of the present invention includes a transparent or translucent housing 12 that supports a fluid inlet needle (first cannula) on one side of the housing and a fluid outlet needle (second cannula) on an opposite side thereof. Fluid collected from the first cannula is immediately visualized through the housing to provide a timely indication of proper vein entry.

Figure 1:
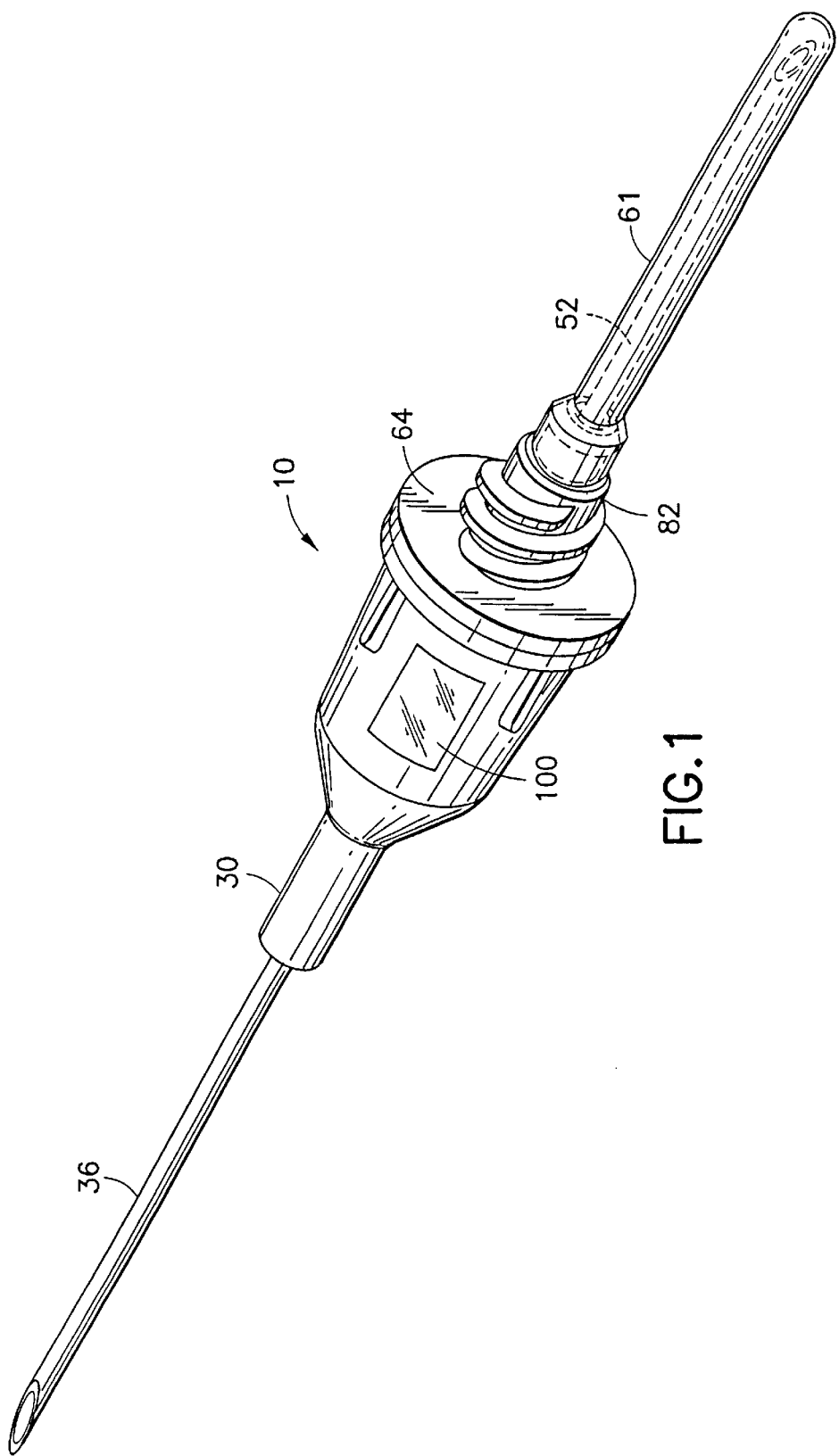
FIG. 1 is a perspective view of the needle assembly of the present invention.

As shown in FIGS. 1–3, needle assembly 10 includes a housing 12 having a fluid inlet end 14 and a fluid outlet end 16. Fluid inlet end 14 is defined by a cylindrical exterior wall 18 having an annular shoulder 20 protruding from an extremity thereof proximate fluid outlet end 16. Wall 18 circumscribes a flashback chamber 22 therein. Chamber 22 further includes an annular trench 26 defined within a frustoconical taper 28 depending outwardly from wall 18.

Fluid inlet end 14 is further defined by an injection end 30 wherein a cylindrical extension 32 is provided. Cylindrical extension 32, having an outer diameter smaller than an inner diameter of wall 18, protrudes outwardly from wall 18 with frustoconical taper 28 providing a bridge therebetween.

Cylindrical extension 32 has a large bore 34 extending therethrough which is sized to accommodate insertion and securement of a first fluid inlet cannula 36 therein. First cannula 36 has an exterior extremity 40 projecting outwardly from injection end 30 and further has a sharpened bevel 42. A first interior extremity 44 is defined at an opposite end of cannula 36 having a blunt tip 46 for insertion of cannula 36 in injection end 30. Bevel 42 and blunt tip 46 each include a correspondingly configured opening for uninterrupted passage of a fluid therethrough.

First cannula 36 is positioned in bore 34 such that first interior extremity 44 lies proximate annular trench 26 so as to remain in fluid communication therewith. Once cannula 36 is positioned properly, it may be frictionally engaged by bore 34 or affixed therein by means of an adhesive or the like.

Bore 34 spans an extent of cylindrical extension 32 and extends into taper 28 so as to be in communication with each of first cannula 36 and a second fluid outlet cannula 52. Second cannula 52, has a second interior extremity 54 with a blunt tip 56. Blunt tip 56 circumscribes the opening within trench 26 so as to be adjacent first interior extremity 44 of first cannula 36. Second cannula 52 further includes an exterior extremity 58 having a non-patient bevel end 60. Second cannula 52 extends outwardly from fluid outlet end 16 so as to form an elongate fluid passageway through housing 12. Non-patient bevel end 60 further includes a sealable sleeve 61 covering exterior extremity 58.

Fluid outlet end 16 of housing 12 includes a disc-like base 64 having a cylindrical protrusion 66 extending outwardly therefrom. Base 64 includes an annular flange 68 which is seated in cooperation with annular shoulder 20 of fluid inlet end 14 so as to form an interface 80 therebetween. The ends may be secured together along interface 80 by appropriate fastening means such as adhesives or the like.

Figure 4:
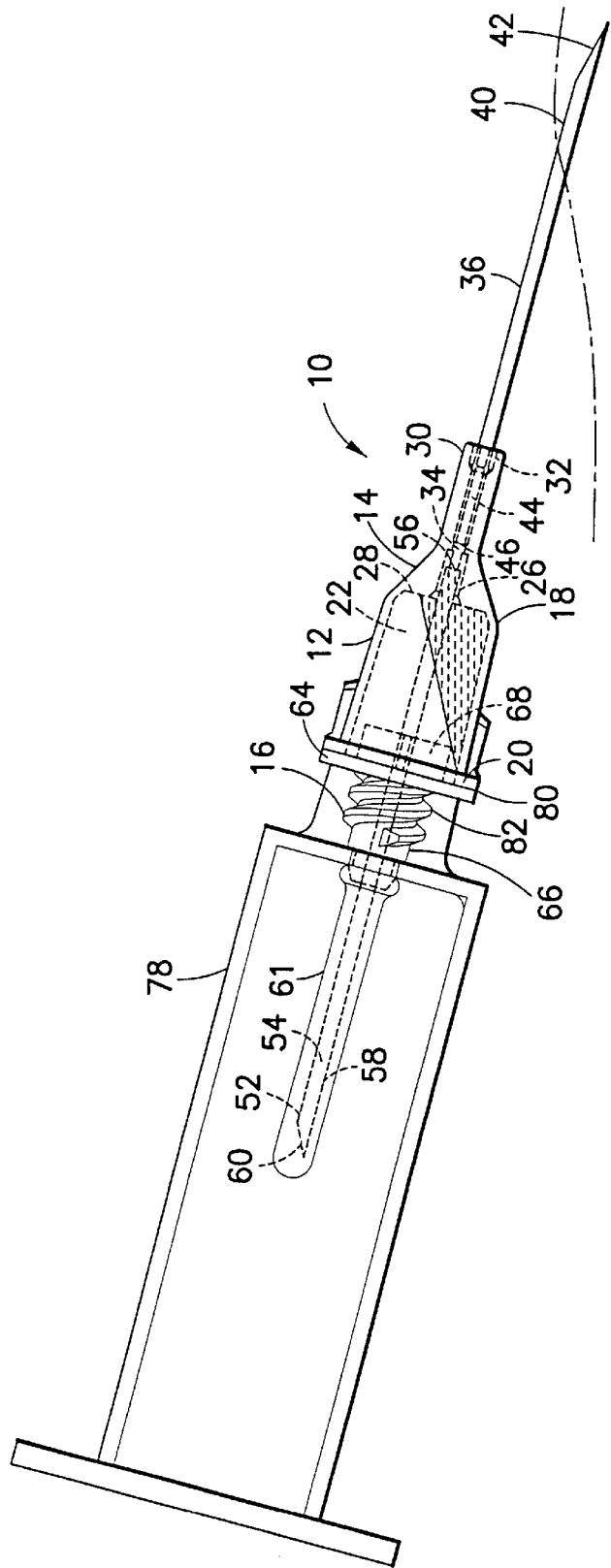
FIG. 4 illustrates the use of the needle assembly of FIG. 1 with a conventional needle holder.

As shown in FIG. 4, fluid outlet end 16 preferably includes means for securing needle assembly 10 to a holder 78. Such means includes a plurality of helical threads 82. Although a system of mating threads is shown herein, it is understood that any attachment means conducive to the practice of the present invention may be utilized.

Housing 12 is constructed from a translucent or transparent material so that a user of the assembly can readily view the contents of chamber 22. Although translucent rigid plastic is desirable, various sealed ports or windows such as window 100 shown in FIG. 2 may be used which enable the user to view the contents within chamber 22.

As shown in FIG. 4, during a conventional venipuncture procedure, needle assembly 10 as connected to holder 78 punctures the patient's skin to make a vein entry. Flashback chamber 22 provides sufficient space in chamber 22 to allow blood to flow beyond the opening of interior extremity 44 into trench 26 for instantaneous flashback visualization in relation to venous entry. In this manner, the phlebotomist has an almost instant visual indication that vein entry has been satisfactorily achieved by first cannula 36. Thus, upon satisfactory vein entry, air that is at atmospheric pressure within chamber 22 experiences compression due to the influence of venous pressure. Because the venous pressure exceeds the atmospheric pressure within chamber 22, blood flows thereinto and covers the opening of second interior extremity 54. Blood flow ceases once the pressure within chamber 22 and the venous pressure are equal.

Figure 5:
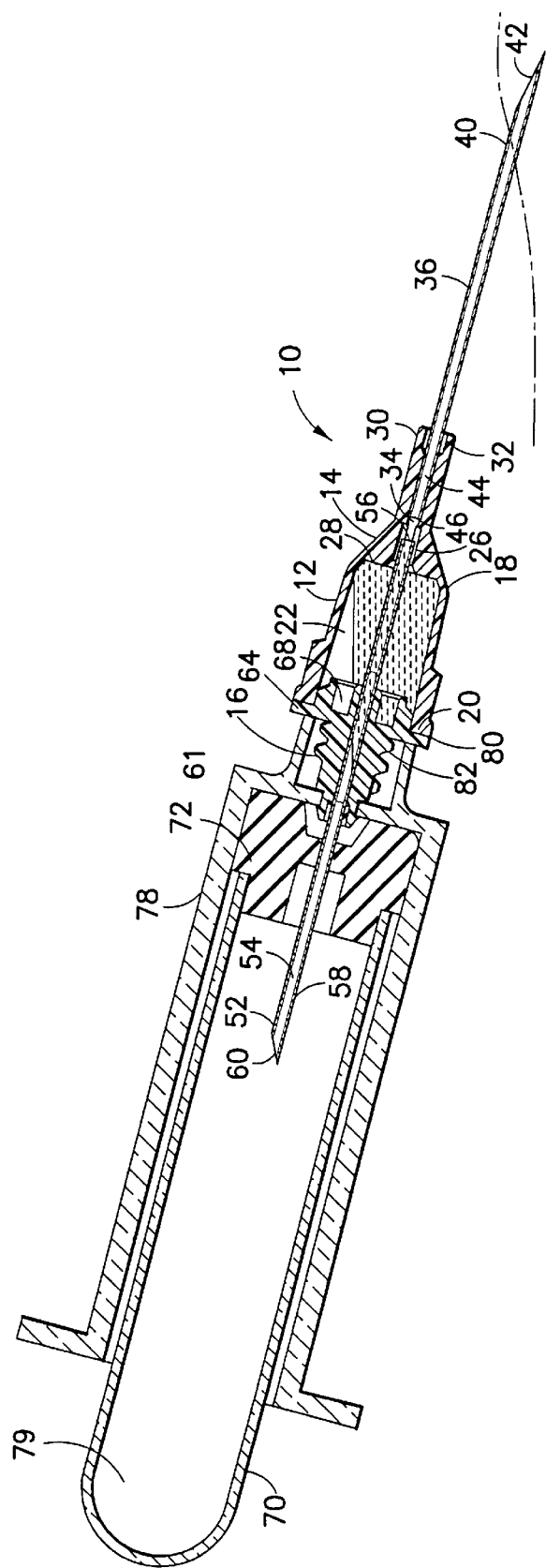
FIG. 5 is a cross-sectional view of the needle assembly in use with a conventional needle holder and a container during venipuncture of a patient's arm.

Once venous entry is visually confirmed by the phlebotomist, container 70, which is evacuated, is then inserted into holder 78 such that bevel 60 of second cannula 52 penetrates stopper 72 as shown in FIG. 5. Upon entrance into a vacuum portion 79 by second cannula 52, a negative pressure gradient is transmitted to the needle assembly. A lower pressure within the container causes blood to flow from the vein and into the container. Because axially aligned cannula 36 and 52 provide an unblocked path for blood flow into container 70, under the influence of the negative pressure gradient. The blood present in trench 26 and chamber 22 is drawn into container 70 through the opening of second interior extremity 54 because of the negative pressure gradient in chamber 22. When this occurs, the pressure within chamber 22 and trench 26 drops below the patient's venous pressure, whereby the higher venous pressure will pressurize trench 26 and chamber 22 back to venous pressure again. The net effect is that a small column of blood, pulsating within trench 26, attempts to close the opening and minimizing air within chamber 22 from being drawn into container 70 by second interior extremity 54. Blood may be collected into multiple evacuated containers so that corresponding multiple samples may be obtained using a single needle assembly 10. The venipuncture procedure is terminated by removal of first cannula 36 from the patient's vein.

Figure 6:
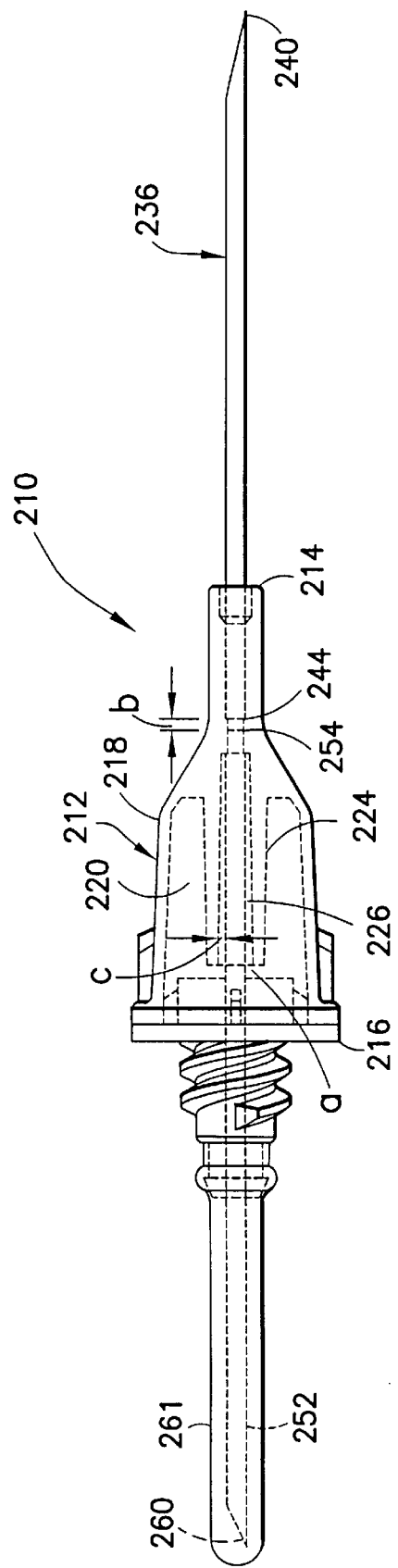
FIG. 6 is a cross-sectional view of an alternate embodiment of the needle assembly of the present invention.
Figure 7:
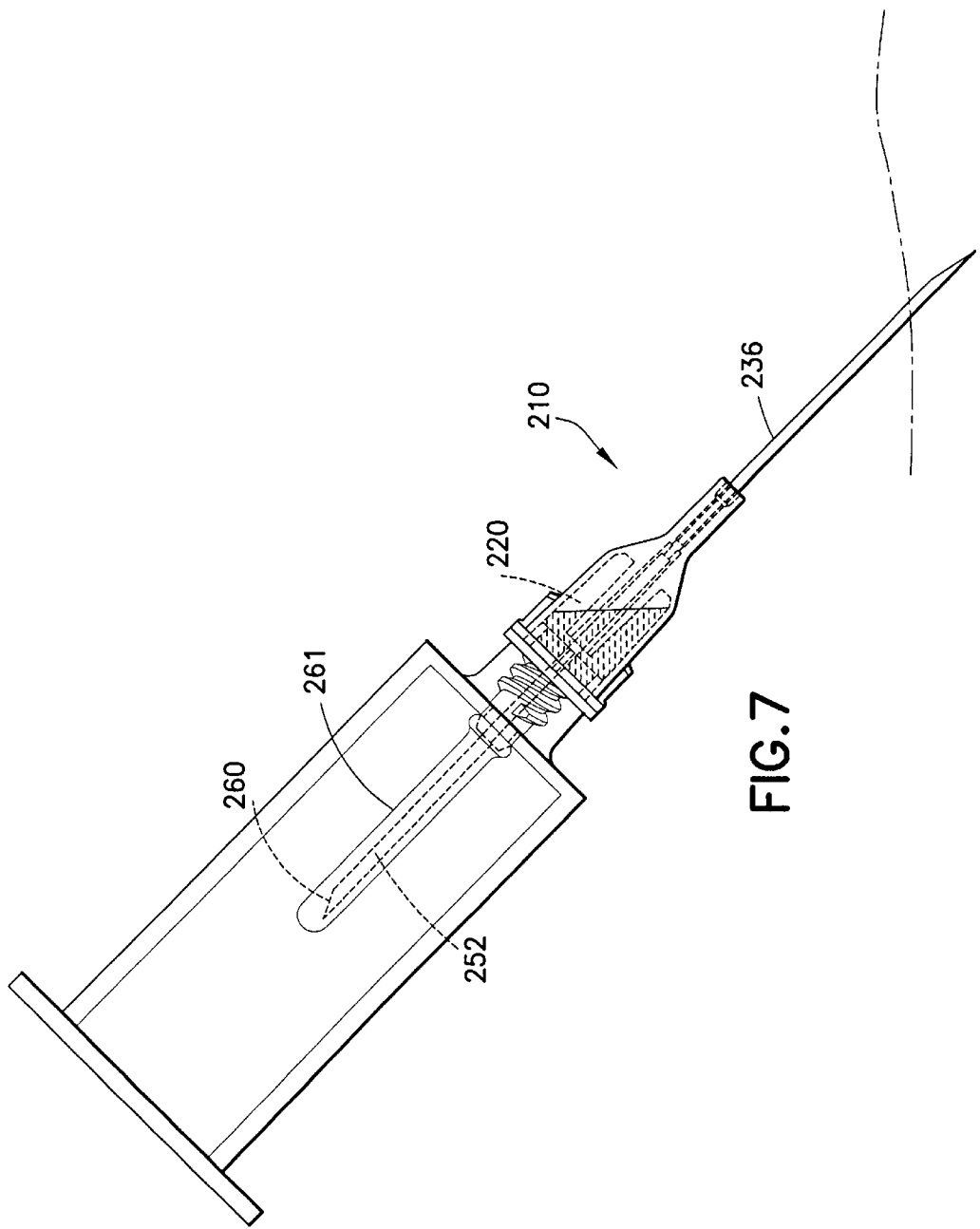
FIG. 7 illustrates the use of the needle assembly of FIG. 6 with a conventional needle holder.
Figure 8:
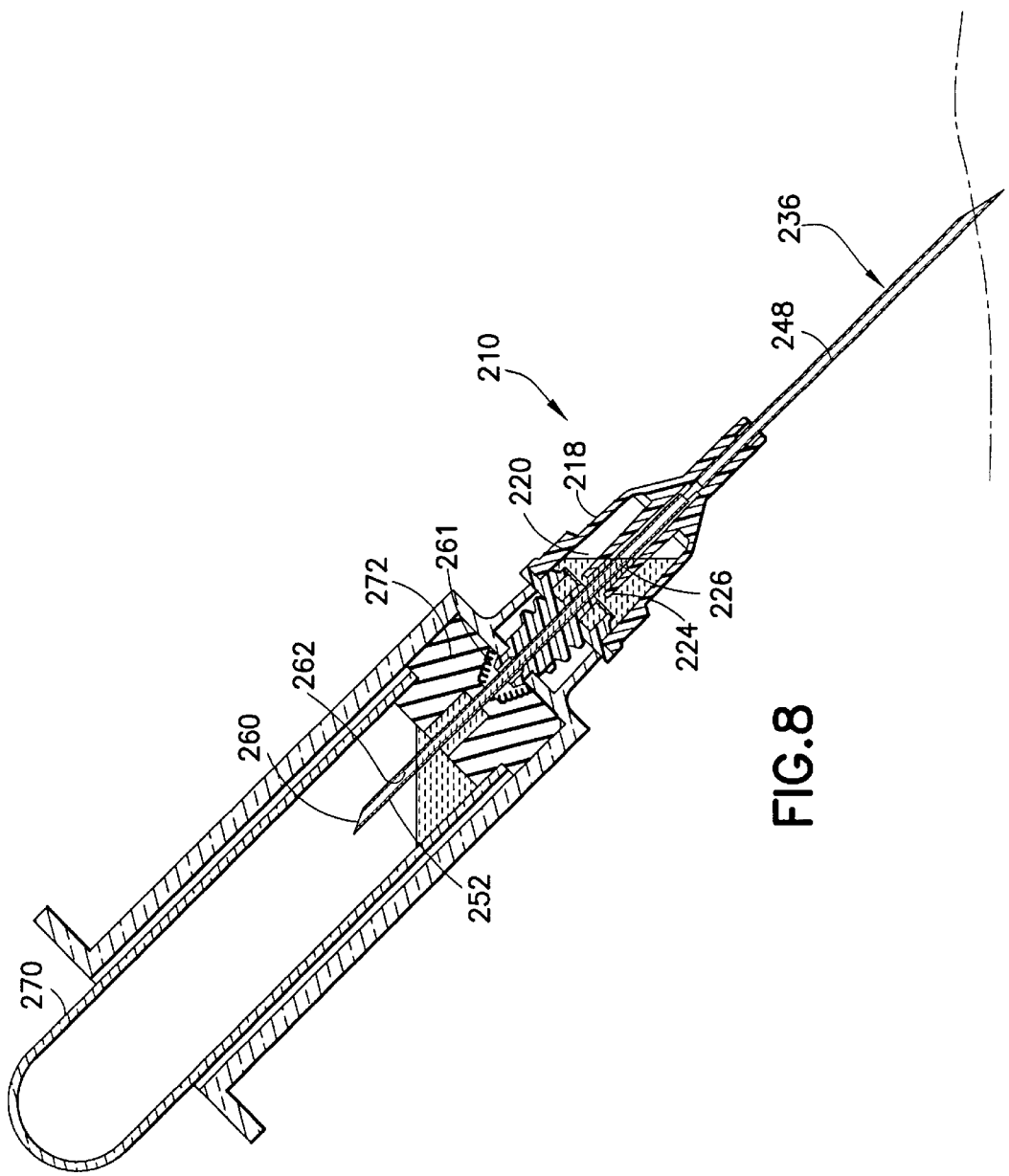
FIG. 8 is a cross-sectional view of the needle assembly in use with a conventional needle holder and a container during venipuncture of a patient's arm.

An additional embodiment of the present invention is shown in FIGS. 6–8, and includes many components which are substantially identical to the components of FIGS. 1–5.

With reference to FIG. 6, the alternate embodiment is directed to a needle assembly 210 with a housing 212 having a fluid inlet end 214, a fluid outlet end 216 and a frustum-shaped exterior wall 218 extending between the ends. Exterior wall 218 defines an outer chamber 220. Housing 212 further includes a cylindrical interior wall 224 that extends in outer chamber 220 from fluid inlet end 214 substantially concentrically with cylindrical exterior wall 218 for a major portion of the distance between fluid inlet end 214 and fluid outlet end 216. The open end of cylindrical interior wall 224 is spaced from outlet end 216 of housing 212 by a distance "a" of only about 1.15 mm. Cylindrical interior wall 224 defines a flashback chamber 226. The elongate flashback chamber 226 behaves like a straw that draws residual blood in housing 212 from the previous draw into a new evacuated tube as explained herein.

Needle assembly 210 also includes a fluid inlet cannula 236 having an exterior end 240 that defines a sharpened bevel and an interior end 244 that is mounted fixedly in fluid inlet end 214 of housing 212. Fluid inlet cannula 236 is characterized further by a substantially cylindrical lumen 248 extending between the ends and communicating with the interior of housing 212.

Needle assembly 210 further includes a fluid outlet cannula 252. Outlet cannula 252 concludes a blunt interior end 254, an exterior end 260 defining a sharpened bevel and a substantially cylindrical lumen 262 extending between the ends. Portions of outlet cannula 252 between the ends are securely affixed in outlet end 216 of housing 212. Outlet cannula 252 is mounted so that interior end 254 passes substantially coaxially into interior wall 224 and so that interior end 254 of outlet cannula 252 substantially aligns axially with interior end 244 of inlet cannula 236. Additionally, interior end 254 of outlet cannula 252 is spaced only a small distance from interior end 244 of inlet cannula 236. This distance "b" between inlet and outlet cannulas 236 and 252 preferably is between 0.5 mm and 1.2 mm and most preferably about 1.0 mm. An axial gap between interior end 254 of outlet cannula 252 and interior end 244 of inlet cannula 236 that is less than 0.5 mm may result in a flashback that is inconsistent. On the other hand, a gap that is greater than 1.2 mm may result in drawing more air from housing 212 into the evacuated tube.

Cylindrical interior wall 224 is dimensioned relative to outlet cannula 252 to achieve both desirable flow of blood through assembly 210 and to achieve effective flashback indication. In particular, cylindrical interior wall 224 preferably is dimensioned to provide a radial gap around outlet cannula 252 of about 0.2 mm, as indicated by dimension "c" in FIG. 6. This gap achieves a substantially laminar blood flow within flashback chamber 226 and prevents blood hemolysis. Additionally, the small radial gap between cylindrical inner wall 224 and outlet cannula 252 enables a drop of blood to be spread thinly across the radial gap in flashback chamber 226 to provide a magnified flashback indication with a very small volume of blood. Thus, an easily visualized flashback indication is achieved quickly at the first appearance of blood from interior end 244 of inlet cannula 236. The small radial gap also has been found to increase surface adhesion between the blood and the inner surface of cylindrical interior wall 224 for further reducing the air draw from housing 212 into the evacuated tube 270 shown in FIG. 8.

Needle assembly 210 further includes a sealable sleeve 261 mounted to fluid outlet end 216 of housing 212 and covering exterior end 258 of outlet cannula 252 when sealable sleeve 261 is in an unbiased condition. However, sealable sleeve 261 can be collapsed in response to pressure exerted by stopper 272 of evacuated tube 270 for urging exterior end 260 of outlet cannula 252 through both sealable sleeve 261 and stopper of 272 evacuated tube 270.

As illustrated in FIG. 7 during a conventional venipuncture, needle assembly 210 is connected to holder 278 and punctures the patient's skin to make a vein entry. Flashback chamber 226 indicates successful vein entry and reduces the draw of air present in housing 212. Thus, upon satisfactory vein entry, air that is at atmospheric pressure within chamber 220 experiences compression due to the influence of venous pressure. Because the venous pressure exceeds the atmospheric pressure within chamber 220, blood flows thereinto. Blood flow ceases once the pressure within chamber 220 and the venous pressure are equal.

Once venous entry is visually confirmed by the phlebotomist, container 270, which is evacuated, is then inserted into holder 278 such that exterior end 260 of second cannula 252 penetrates stopper 272 as shown in FIG. 8. Upon entrance into vacuum portion 279 by second cannula 252, a negative pressure gradient is transmitted to chambers 220 and 226. A lower pressure within the container 270 causes blood to flow from chambers 220 and 226 into the container 270.

The needle assemblies described above desirably should be small for convenient use, but should constructed to ensure reliable and rapid flashback. The occurrence of flashback in the needle assemblies described and illustrated above operate pursuant to the ideal gas law. In particular, at very low densities all gases and vapors approach ideal gas behavior and closely follow the Boyle's and Charles' laws given by:

$$P_1 V_1 = P_2 V_2$$

where $P_1$ denotes the pressure of air within the needle assembly before needle insertion, $P_2$ denotes the pressure of air within the needle assembly after vein entry;

$V_1$ denotes the volume of air within the needle assembly before vein entry; and $V_2$ denotes the volume of air within the needle assembly after vein entry.

Figure 9:
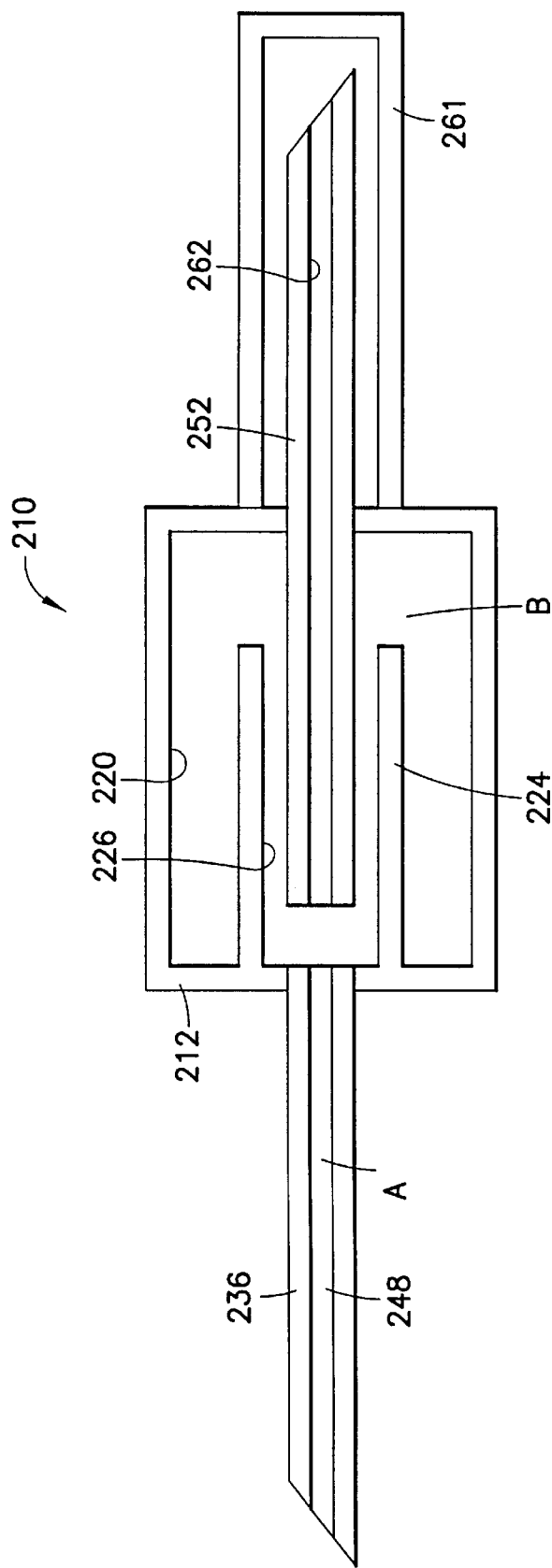
FIG. 9 is a schematic view of the needle assembly of FIG. 6 prior to use.
Figure 10:
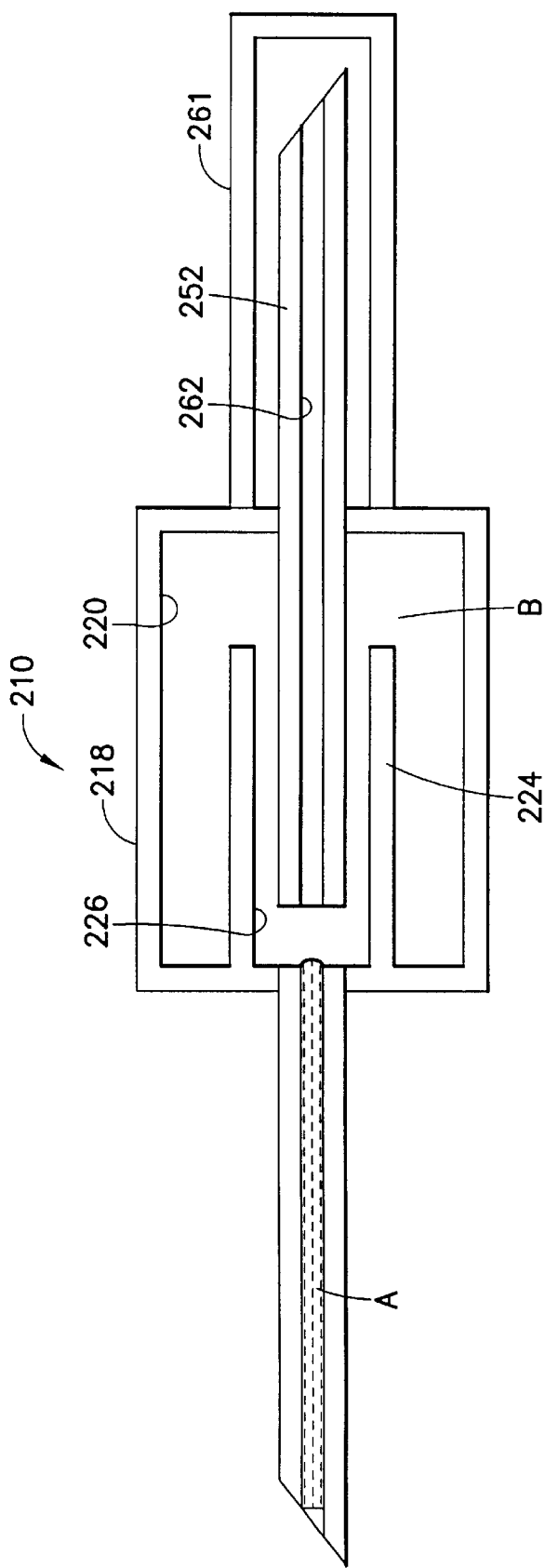
FIG. 10 is a schematic view similar to FIG. 9, but showing the first sign of venous entry.

Design parameters should keep the needle device as small as possible for easy use, while ensuring an appropriate volume as specified by the preceding equation. FIGS. 9 and 10 provide schematic representations of the needle assembly 210 of FIGS. 6–8 for purposes of depicting the application of the ideal gas law. In this regard, A identifies the volume of lumen 248 thought inlet cannula 236. B denotes the total volume of outer chamber 220, inner chamber 226, lumen 262 through outlet cannula 252 and sealable sleeve 261. Referring again to the preceding equation, $P_1$ is the pressure within needle assembly 210 before use, and hence substantially equals atmospheric pressure. Atmospheric pressure will vary slightly from time to time and from location to location. However, for purposes of this analysis, atmospheric pressure $P_1$ will be assumed to be 760 mm Hg. $P_2$ in the preceding equation is the volume of the dead space in needle assembly 210 after vein entry. More particularly, after vein entry, blood will fill lumen 248 of inlet cannula 236, thereby reducing the volume to be occupied by gas in remaining portions of needle assembly 210 and hence increasing the pressure of air in the remaining portion of needle assembly 210. A needle assembly with dimensions approximately as shown in FIGS. 6–10 will have a pressure $P_2$ of about 790 mm Hg at venous pressure (with tourniquet). $V_1$ in the preceding equation defines the volume of the total dead spaced in needle assembly 210 before use, and hence will equal A+B as shown in FIG. 9. $V_2$ defines the dead space in the device after vein entry, and with lumen 248 of inlet cannula 236 filled with blood, as shown in FIG. 10. Hence, $V_2$ in the preceding equation will equal B. These input parameters can be employed to define a minimum desired size for the respective components of needle assembly 200 as shown in the following application of the ideal gas law equation.

$$P_1 V_1 = P_2 V_2$$

$$P_1/P_2 = V_2/V_1$$

$$760/790 = B/(A+B)$$

$$0.962 = B/(A+B)$$

$$0.962(A+B) = B$$

$$0.038B = 0.962A$$

$$B = 25.3A$$

Therefore, dead space in housing 212, outlet cannula 252 and sleeve 261 preferably is at least 25.3 times the volume defined by lumen 248 through inlet cannula 236, and most preferably is about 26 times the volume of lumen 248.

Upon satisfactory vein entry, air within housing 212 is compressed under the influence of venous pressure, thereby allowing blood to flow into inner chamber 220 for visualization. Blood flow stops once pressure within housing 212 equals the venous pressure, covering inner end 254 of outlet cannula 252.

The immediate response when an evacuated tube is placed in communication with outlet cannula 252 is to draw blood and air from the vein and housing 212 into tube 270, as shown in FIG. 8. The highest pressure gradient is always maintained between the vein and the evacuated tube 270. The axially aligned inlet cannula 236 and outlet cannula 252 provided an unobstructed path for blood flow from the vein into evacuated tube 270. Conversely, air in housing 212 has tortuous path to outlet cannula 252 and the flow of air from housing 212 to outlet cannula 252 is detoured by the axially unobstructed blood flow between inlet and outlet cannula 236 and 252 respectively. The moment some air in housing 212 is drawn into the evacuated tube 270, pressure within housing 212 drops below the venous pressure. Accordingly, more air loss is prevented until housing 212 is pressurized back venous pressure, and blood flows in flashback chamber 226 until the pressure in housing 212 equals the venous pressure. The above described pressurization and depressurization dynamics within housing 212 results in column of blood pulsating in flashback chamber 226, and hence minimizing air draw into the evacuated tube 270.

Figure 11:
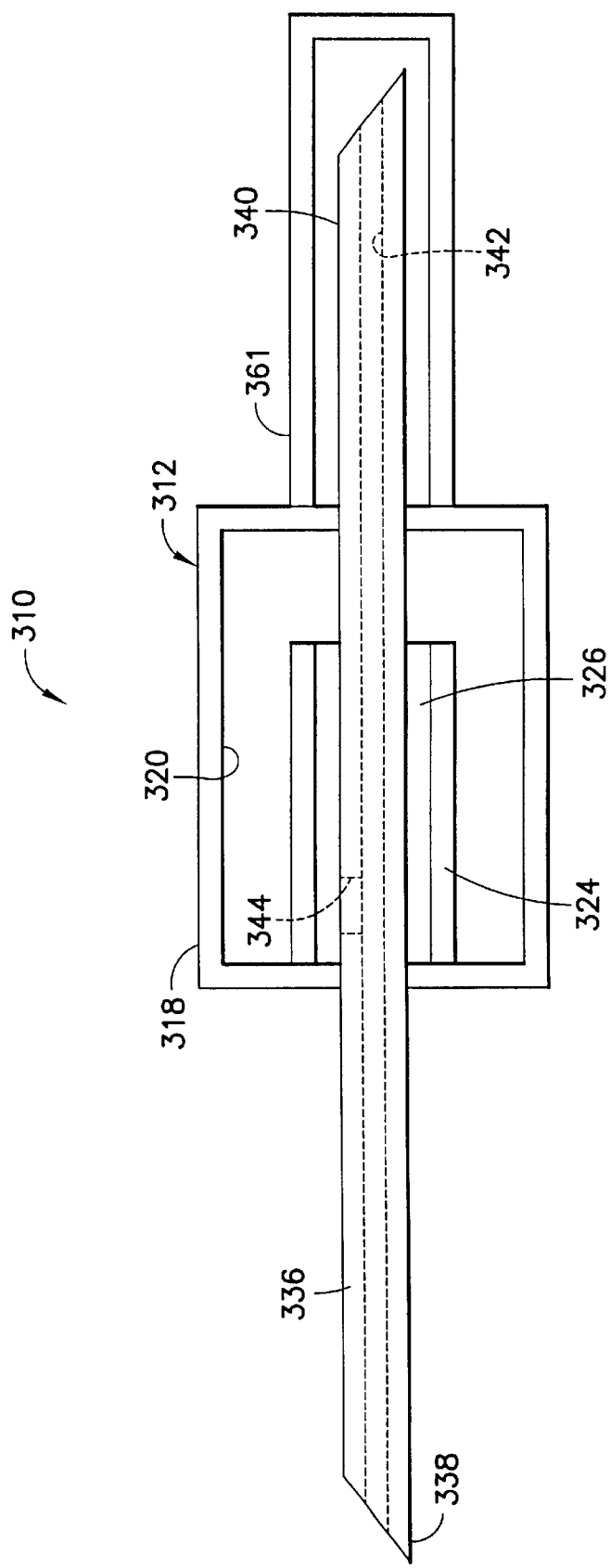
FIG. 11 is a schematic view of a third embodiment.

The preceding embodiments show structurally separate inlet and outlet cannulas that are axially aligned with one other and placed in close end-to-end relationship with one another. However, the principals of the invention described above also can be achieved with a single cannula formed with a transverse slot or aperture within the flashback chamber. For example, FIG. 11 schematically shows a needle assembly 310 with a housing 312 that is substantially identical to housing 212 described and illustrated above. Needle assembly 310 differs from needle assembly 210 in that a single double end needle cannula 336 is provided and passes entirely through housing 312. More particularly, needle cannula 336 includes a venous entry end 338, a non-patient end 340 and a lumen 342 extending therebetween. Portions of cannula 336 within inner wall 324 include a slot or aperture 344 to provide communication between lumen 342 and flashback chamber 336 within inner wall 324. Needle assembly 310 functions substantially in the same manner as needle assembly 210 described and illustrated above.

Although the relative dimensional calculations, volumes and pressures were carried out with respect to the second embodiment, the same theory applied to the first embodiment, and to other unillustrated needle assemblies with a flashback chamber. Accordingly, the scope of the as defined by the appending claims is not limited to the specific illustrated embodiments. Various other changes and modifications may be effected therein by one skilled in the art without departing from the scope or spirit of the invention, and it is intended to claim all such changes and modifications as fall within the scope of the invention.

What is claimed is:

1. A needle assembly comprising:
a housing having an inlet end, an outlet end and a chamber formed between said ends;
an inlet cannula having opposite external and internal ends and a lumen extending between said ends, said inlet cannula being mounted to said housing such that said external end of said inlet cannula is externally of said housing and such that said lumen through said inlet cannula communicates with said chamber;
an outlet cannula having opposite internal and external ends and a lumen extending between said ends, said outlet cannula being mounted to said housing such that said external end of said outlet cannula is externally of said housing and such that said lumen of said outlet cannula communicates with said chamber;
a sealable sleeve mounted over portions of said outlet cannula disposed externally of said housing; and
wherein said sealable sleeve, said lumen of said outlet cannula and said chamber of said housing define a combined volume approximately 26 times greater than a volume defined by said lumen of said inlet cannula for achieving a rapid indication of venous entry adjacent said external end of said inlet cannula.

2. A needle assembly comprising:
a housing having an inlet end, an outlet end and a chamber formed between said ends;
an inlet cannula having opposite external and internal ends and a lumen extending between said ends, said inlet cannula being mounted to said housing such that said external end of said inlet cannula is externally of said housing and such that said lumen through said inlet cannula communicates with said chamber;
an outlet cannula having opposite internal and external ends and a lumen extending between said ends, said outlet cannula being mounted to said housing such that said external end of said outlet cannula is externally of said housing and such that said lumen of said outlet cannula communicates with said chamber;
a sealable sleeve mounted over portions of said outlet cannula disposed externally of said housing; and
wherein said sealable sleeve, said lumen of said outlet cannula and said chamber define a combined volume that is at least equal to a product of a pre-use volume of said needle assembly multiplied by a ratio of pressure in said needle assembly prior to use and pressure in said needle assembly when said lumen of said inlet cannula is filled with fluid for achieving a rapid indication of venous entry adjacent said external end of said inlet cannula.

3. The needle assembly of claim 1, wherein said lumen of the said inlet cannula is substantially axially aligned with said lumen of said outlet cannula.

4. A needle assembly comprising:
a housing having an inlet end, an outlet end and a chamber formed between said ends;
an inlet cannula having opposite external and internal ends and a lumen extending between said ends, said inlet cannula being mounted to said housing such that said external end of said inlet cannula is externally of said housing and such that said lumen through said inlet cannula communicates with said chamber;
an outlet cannula having opposite internal and external ends and a lumen extending between said ends, said outlet cannula being mounted to said housing such that said external end of said outlet cannula is externally of said housing and such that said lumen of said outlet cannula communicates with said chamber, said lumen of said outlet cannula being substantially axially aligned with said lumen of said inlet cannula, and
wherein said inlet cannula is spaced from said outlet cannula by a distance of between approximately 0.5 mm and 1.2 mm;

a sealable sleeve mounted over portions of said outlet cannula disposed externally of said housing; and wherein said sealable sleeve, said lumen of said outlet cannula and said chamber of said housing define a combined volume approximately 26 times greater than a volume defined by said lumen of said inlet cannula for achieving a rapid indication of venous entry adjacent said external end of said inlet cannula.

5. The needle assembly of claim 4, wherein said inlet cannula is spaced from said outlet cannula by a distance by approximately 1.0 mm.

6. A needle assembly comprising:

a housing having an inlet end, an outlet end and a chamber formed between said ends;

an inlet cannula having opposite external and internal ends and a lumen extending between said ends, said inlet cannula being mounted to said housing such that said external end of said inlet cannula is externally of said housing and such that said lumen through said inlet cannula communicates with said chamber;

an outlet cannula having opposite internal and external ends and a lumen extending between said ends, said outlet cannula being mounted to said housing such that said external end of said outlet cannula is externally of said housing and such that said lumen of said outlet cannula communicates with said chamber, said lumen of said outlet cannula being substantially axially aligned with said lumen of said inlet cannula, and further comprising a flashback chamber wall extending from said inlet end of said housing and disposed within said chamber, said flashback chamber wall surrounding said interior end of said inlet cannula and said interior end of said outlet cannula;

a sealable sleeve mounted over portions of said outlet cannula disposed externally of said housing; and wherein said sealable sleeve said lumen of said outlet cannula and said chamber of said housing define a combined volume approximately 26 times greater than a volume defined by said lumen of said inlet cannula for achieving a rapid indication of venous entry adjacent said external end of said inlet cannula.

7. The needle assembly of claim 6, wherein said flashback chamber wall is dimensioned to define a radial gap around said inlet cannula and said outlet cannula of approximately 0.2 mm.

8. The needle assembly of claim 7, said flashback chamber wall extends a major portion of a distance between said inlet and outlet ends of said housing.

9. The needle assembly of claim 8, wherein said flashback chamber wall is spaced from said outlet end of said housing by distance of about 1.15 mm.

10. The needle assembly of claim 9, wherein said inlet cannula is spaced from said outlet cannula by a distance of between approximately 0.5 mm and 1.2 mm.

11. A needle comprising:

a housing having an inlet end, an outlet end and a chamber formed between said ends;

an inlet cannula having opposite external and internal ends and a lumen extending between said ends, and inlet cannula being mounted to said housing such that said external end of said inlet cannula is externally of said housing and such that said lumen through said inlet cannula communicates with said chamber;

an outlet cannula having opposite internal and external ends and a lumen extending between said ends, said outlet cannula being mounted to said housing such that said external end of said outlet cannula is externally of said housing and such that said lumen of said outlet cannula communicates with said chamber;

a sealable sleeve mounted over portions of said outlet cannula disposed externally of said housing;

wherein said sealable sleeve, said lumen of said outlet cannula and said chamber of said housing define a combined volume approximately 26 times greater than a volume defined by said lumen of said inlet cannula for achieving a rapid indication of venous entry adjacent said external end of said inlet cannula; and wherein said housing includes an inlet end wall at said inlet end of said housing, said inlet cannula being securely mounted in said inlet end wall, portions of said inlet end wall between said inlet cannula and said chamber defining a trench, said outlet cannula extending through said chamber such that said internal end of said outlet cannula is in said trench.

12. The needle assembly of claim 11, wherein the trench is dimensioned to define an annular space surrounding portions of said outlet cannula extending into said trench.

13. The needle assembly of claim 1, wherein said housing is free of air vents.

14. A blood collection needle assembly comprising:

a housing having an inlet end wall, an outlet end wall and a substantially tubular external wall extending between said inlet and outlet end walls for defining a vent-free chamber, a substantially tubular flashback chamber wall extending from said inlet end wall toward said outlet end wall, at least portions of said tubular exterior wall and said flashback chamber wall being formed from a substantially transparent material;

an inlet cannula having opposite external and internal ends and a lumen extending between said ends, said inlet cannula being mounted in said inlet end wall such that said external end of said inlet cannula is externally of said housing and such that said lumen through said inlet cannula communicates with portions of said chamber bounded by said flashback chamber wall;

an outlet cannula having opposite internal and external ends and a lumen extending between said ends, said outlet cannula being mounted in said outlet end wall such that said external end of said outlet cannula is externally of said housing and said internal end of said outlet cannula is aligned with said internal end of said inlet cannula;

a sealable sleeve mounted over portions of said outlet cannula disposed externally of said housing; and wherein said chamber is formed to define a volume relative to volumes of said sealable sleeve, said lumen of said outlet cannula and said lumen of said inlet cannula for achieving a rapid indication of venous entry in areas bounded by said flashback chamber wall.

15. The blood collection needle assembly of claim 14, wherein said combined volume of said sealable sleeve, said lumen of said outlet cannula and said chamber is approximately 26 times said volume of said lumen of said inlet cannula.

16. The blood collection needle assembly of claim 15, wherein said inlet cannula is spaced from said outlet cannula by a distance of between approximately 0.5 mm and 1.2 mm.

17. The blood collection needle assembly of claim 16, wherein said flashback chamber wall is dimensioned to define a radial gap around said inlet cannula and said outlet cannula of approximately 0.2 mm.

* * * * *